(12) United States Patent
Eidenschink

(10) Patent No.: US 7,128,868 B2
(45) Date of Patent: *Oct. 31, 2006

(54) BALLOON WING FORMING APPARATUS AND METHOD

(75) Inventor: Thomas C. Eidenschink, Rogers, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 573 days.

This patent is subject to a terminal disclaimer.

(21) Appl. No.: 10/340,819

(22) Filed: Jan. 10, 2003

(65) Prior Publication Data

US 2004/0135281 A1  Jul. 15, 2004

(51) Int. Cl.
*B29C 35/08* (2006.01)
*B29C 53/08* (2006.01)

(52) U.S. Cl. .................. 264/442; 264/479; 264/69

(58) Field of Classification Search .............. 264/69, 264/442, 479; 425/174.2, 392, 522
See application file for complete search history.

(56) References Cited

U.S. PATENT DOCUMENTS

| | | | | |
|---|---|---|---|---|
| 3,392,219 A * | 7/1968 | Vernon et al. | ............... | 264/442 |
| 4,276,874 A | 7/1981 | Wolvek et al. | ............... | 128/1 D |
| 4,573,470 A | 3/1986 | Samson et al. | ............... | 128/344 |
| 4,576,142 A | 3/1986 | Schiff | ............... | 128/1 D |
| 4,681,092 A | 7/1987 | Cho et al. | ............... | 128/1 D |
| 4,710,181 A | 12/1987 | Fuqua | ............... | 604/280 |
| 4,762,129 A | 8/1988 | Bonzel | ............... | 128/344 |
| 4,771,776 A | 9/1988 | Powell et al. | ............... | 128/344 |
| 4,952,357 A | 8/1990 | Euteneuer | ............... | 264/129 |
| 5,087,246 A | 2/1992 | Smith | ............... | 604/96 |
| 5,147,302 A | 9/1992 | Euteneuer et al. | ............... | 604/103 |
| 5,202,065 A * | 4/1993 | Lenander et al. | ............... | 264/442 |
| 5,226,887 A | 7/1993 | Farr et al. | ............... | 604/96 |
| 5,250,069 A | 10/1993 | Npbuyoshi et al. | ............... | 606/192 |
| 5,350,361 A | 9/1994 | Tsukashima et al. | ............... | 604/96 |
| 5,456,666 A | 10/1995 | Campbell et al. | ............... | 604/96 |
| 5,458,572 A | 10/1995 | Campbell et al. | ............... | 604/96 |
| 5,478,319 A * | 12/1995 | Campbell et al. | ............... | 604/103.08 |
| 5,484,411 A | 1/1996 | Inderbitzen et al. | ............... | 604/96 |
| 5,718,684 A | 2/1998 | Gupta | ............... | 604/96 |
| 5,759,172 A | 6/1998 | Weber et al. | ............... | 604/96 |
| 5,783,227 A * | 7/1998 | Dunham | ............... | 425/318 |
| 5,792,172 A | 8/1998 | Fischell et al. | ............... | 606/198 |
| 5,836,965 A | 11/1998 | Jendersee et al. | ............... | 606/198 |
| 5,853,389 A | 12/1998 | Hijkema | ............... | 604/96 |
| 5,913,861 A | 6/1999 | Trotta | ............... | 606/108 |
| 6,013,055 A | 1/2000 | Bampos et al. | ............... | 604/96 |
| 6,033,380 A | 3/2000 | Butaric et al. | ............... | 604/96 |
| 6,283,743 B1 | 9/2001 | Traxler et al. | ............... | 425/391 |
| 6,425,882 B1 | 7/2002 | Vigil | ............... | 604/99.01 |
| 6,428,568 B1 | 8/2002 | Gaudoin et al. | ............... | 623/1.11 |
| 2004/0181236 A1* | 9/2004 | Eidenschink et al. | ............... | 606/108 |

* cited by examiner

*Primary Examiner*—Suzanne E. McDowell
(74) *Attorney, Agent, or Firm*—Vidas, Arrett, Steinkraus

(57) ABSTRACT

An apparatus and method for shaping at least a portion of a medical balloon comprise a balloon shaping device capable of applying a radial inward force to at least a portion of the medical balloon and at least one vibratory device capable of applying vibratory energy to the at least a portion of the medical balloon.

10 Claims, 6 Drawing Sheets

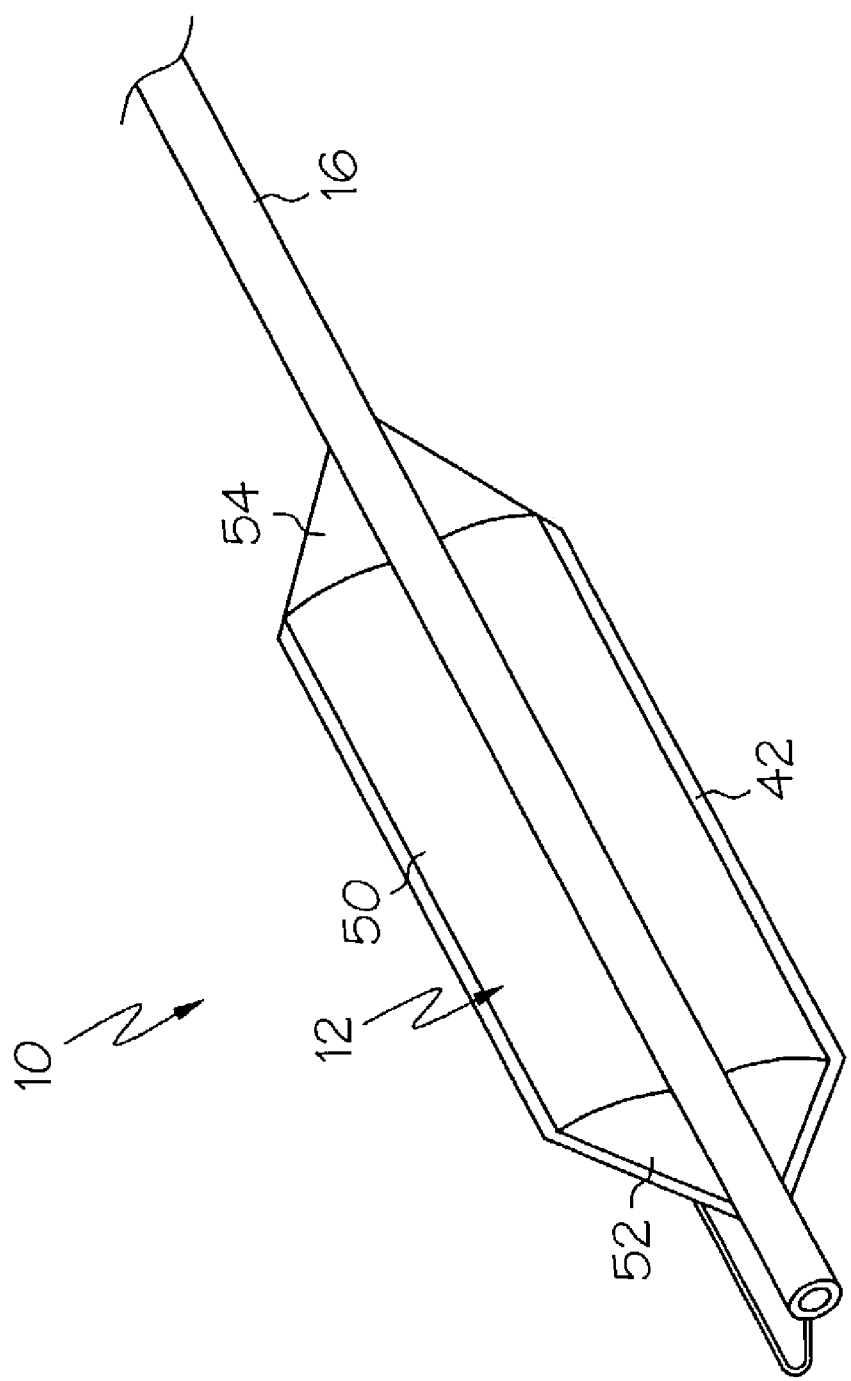

BALLOON WING FORMING APPARATUS AND METHOD

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Medical balloons are used in the body in a variety of applications including as dilatation devices for compressing plaque and for expanding prosthetic devices such as stents at a desired location in a bodily vessel. Because it is typically necessary for the balloon to traverse a tortuous anatomy as it is being delivered to the desired location in the bodily vessel, it is desirable for the balloon to assume as low a profile as possible.

One way to achieve a low profile is by folding the balloon to form a number of wings. Some examples of methods of forming wings on a balloon are described in U.S. Pat. Nos. 5,147,302 and 5,350,361. A common method employed to form wings on a balloon is to partially inflate a balloon and then impart an inward radial force about the periphery of the balloon using a plurality of members or "blades" which are distributed about the periphery of the balloon. As the blades move radially inward, wings are formed in the balloon.

When forming wings in balloons in this manner, however, special care must be taken to ensure that the blades do not have any sharp edges or burrs which would damage the balloon. To this end, some prior balloon folding apparatuses have blades that are equipped with a relatively soft tip of silicone or other material. However, providing the blade with a relatively soft tip may be insufficient to reduce the potential from damage to the balloon during wing formation. In addition to the above, as the tip of each blade pushes radially against the balloon, inconsistent frictional interface between each tip and the balloon material upon which they push may lead to the formation of wings having non-uniform lengths. Balloons having wings of non-uniform lengths may lead to a catheter having a larger profile when the wings are folded.

In prior folding techniques caution must be exercised to prevent the blades from applying damaging forces to the balloon and/or any structures underlying the balloon such as marker bands, bonds or hubs. Although the amount of force applied to the balloon may be reduced to avoid damaging the balloon and/or any underlying structures, sufficient force must, nevertheless, be applied to completely form the balloon wings so as to achieve the desired cross-section. Complete formation of the wing includes imparting one or more creases into each wing. The creases help the balloon to attain a reduced profile by providing wings that are relatively flat and thus are easily folded to provide the balloon with a reduced diameter. Prior methods that form the wings by closing the blades about the balloon may be insufficient to provide creases which are adequate.

In light of the above, it is a goal of the present invention to provide a wing forming method and apparatus that reduces the friction between the balloon and blades, provides for improved ability to produce wings having uniform lengths and/or provides for improved crease formation.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. For example, in at least one embodiment the invention is directed to a method for forming balloon wings, wherein the method employs vibrational energy to aid in wing formation.

In some embodiments the invention is directed to a balloon wing forming apparatus. One or more portions of the apparatus is equipped with one or more transducers that may be excited to impart a vibration to at least a portion of the apparatus. In some embodiments, the vibration has an ultrasonic frequency.

In at least one embodiment the apparatus employs a plurality of members or blades which are constructed and arranged to push radially inward against the balloon to form the wings.

In at least one embodiment the apparatus employs a plurality of inflatable members which when inflated are constructed and arranged to push radially inward against the balloon to form the wings.

Application of vibratory energy to at least portion of the wing forming apparatus reduces the friction between at least the portion of the apparatus contacting the balloon to form the wings. The reduction in friction between the wing forming apparatus and the balloon will reduce potential damage to the balloon that may otherwise occur as a result of contact between the balloon and apparatus during wing formation.

In some embodiments, application of vibratory energy to the wing forming apparatus may aid in forming balloon wings that are substantially uniform in length.

In some embodiments application of vibrations to the wing forming apparatus may aid in providing improved creasing of the balloon wings in the body region of the balloon and/or the cone regions of the balloon.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 9 is a perspective view of a balloon formed in accordance with an embodiment of the invention.

DETAILED DESCRIPTION OF THE INVENTION

Figure 1:
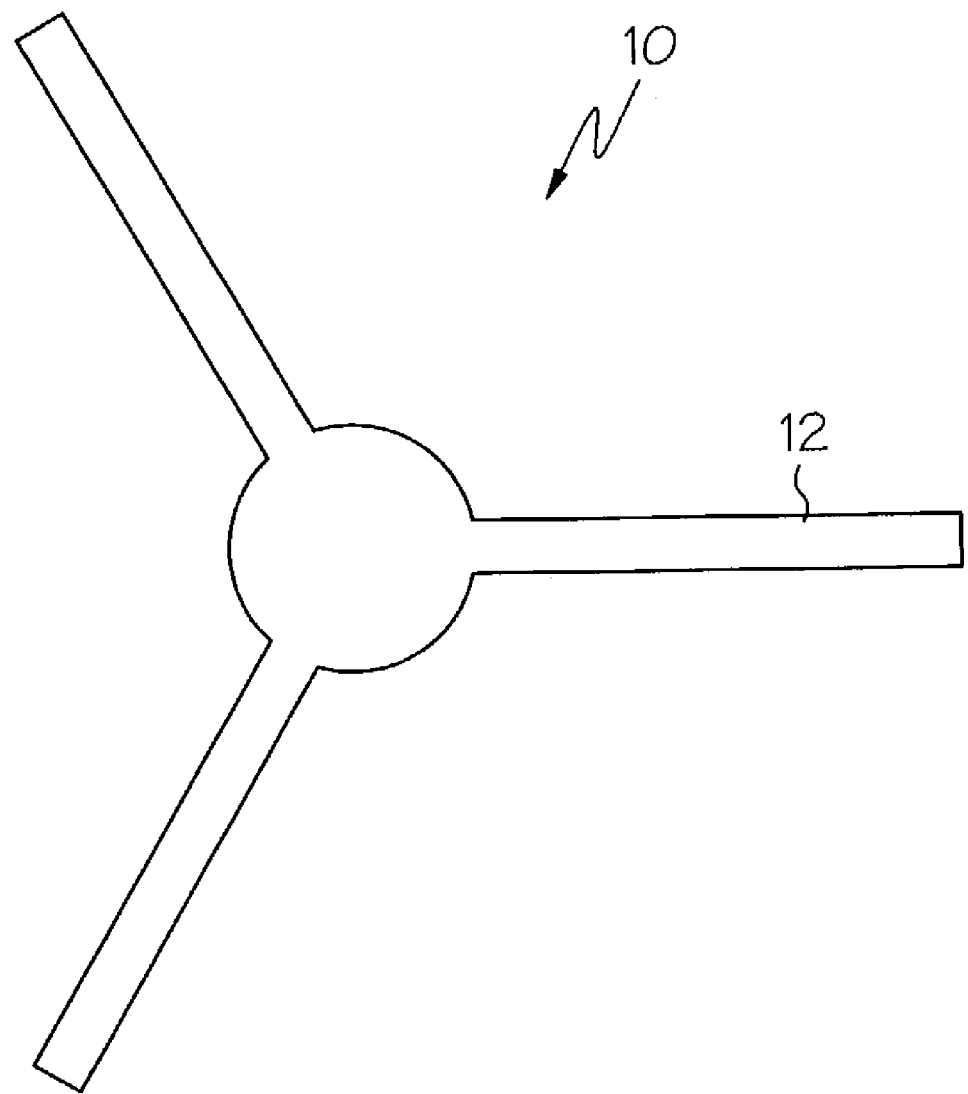
FIG. 1 is a cross-sectional view of a balloon formed in accordance with an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above the present invention is embodied in a variety of forms. In at least one embodiment, the invention is directed to one or more methods of forming at least one fold or wing 12 in a balloon catheter 10, such as is shown in FIG. 1, wherein the methods utilize vibrations in the wing formation process.

Figure 2:
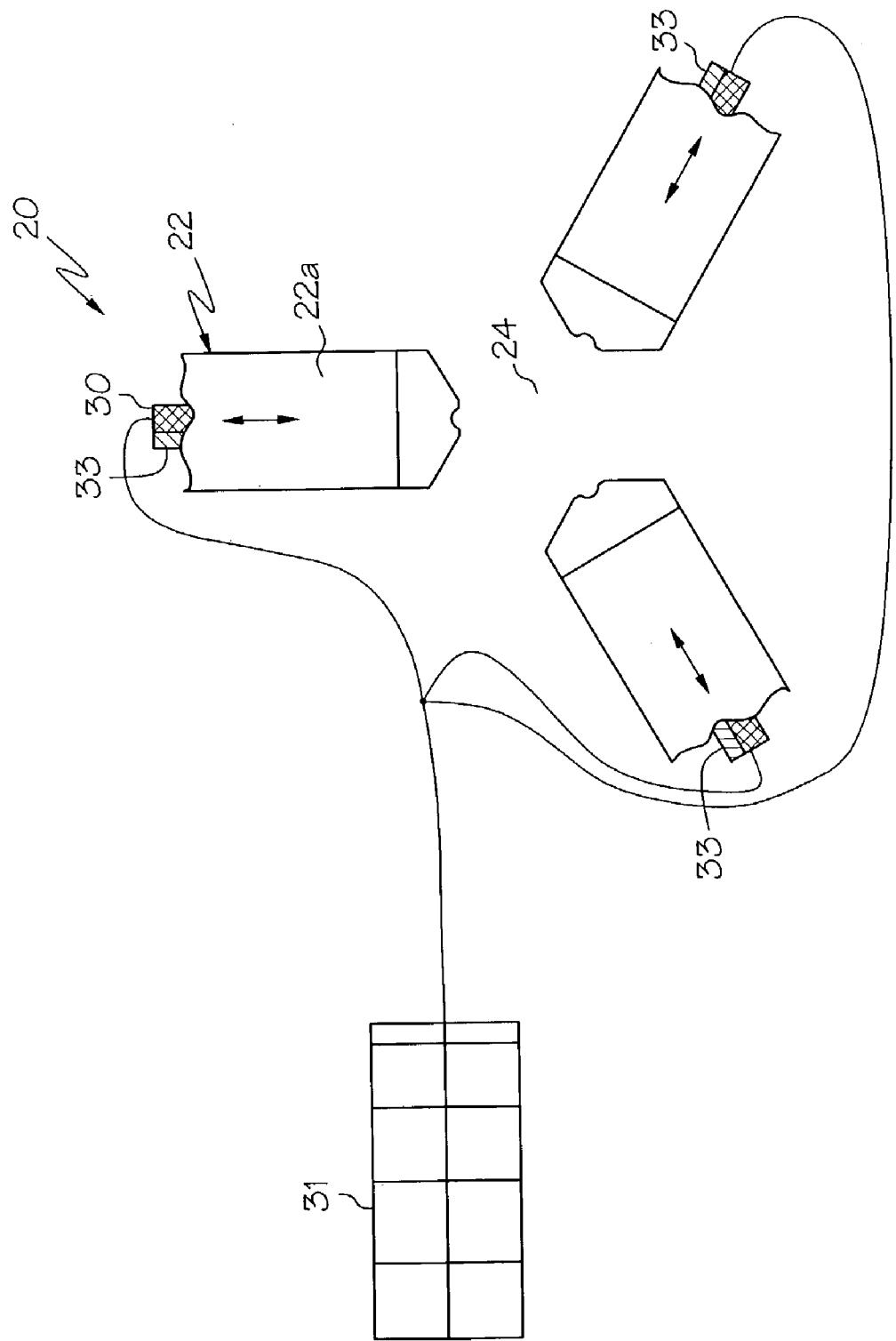
FIG. 2 is a cross-sectional view of an embodiment of the invention.
Figure 3:
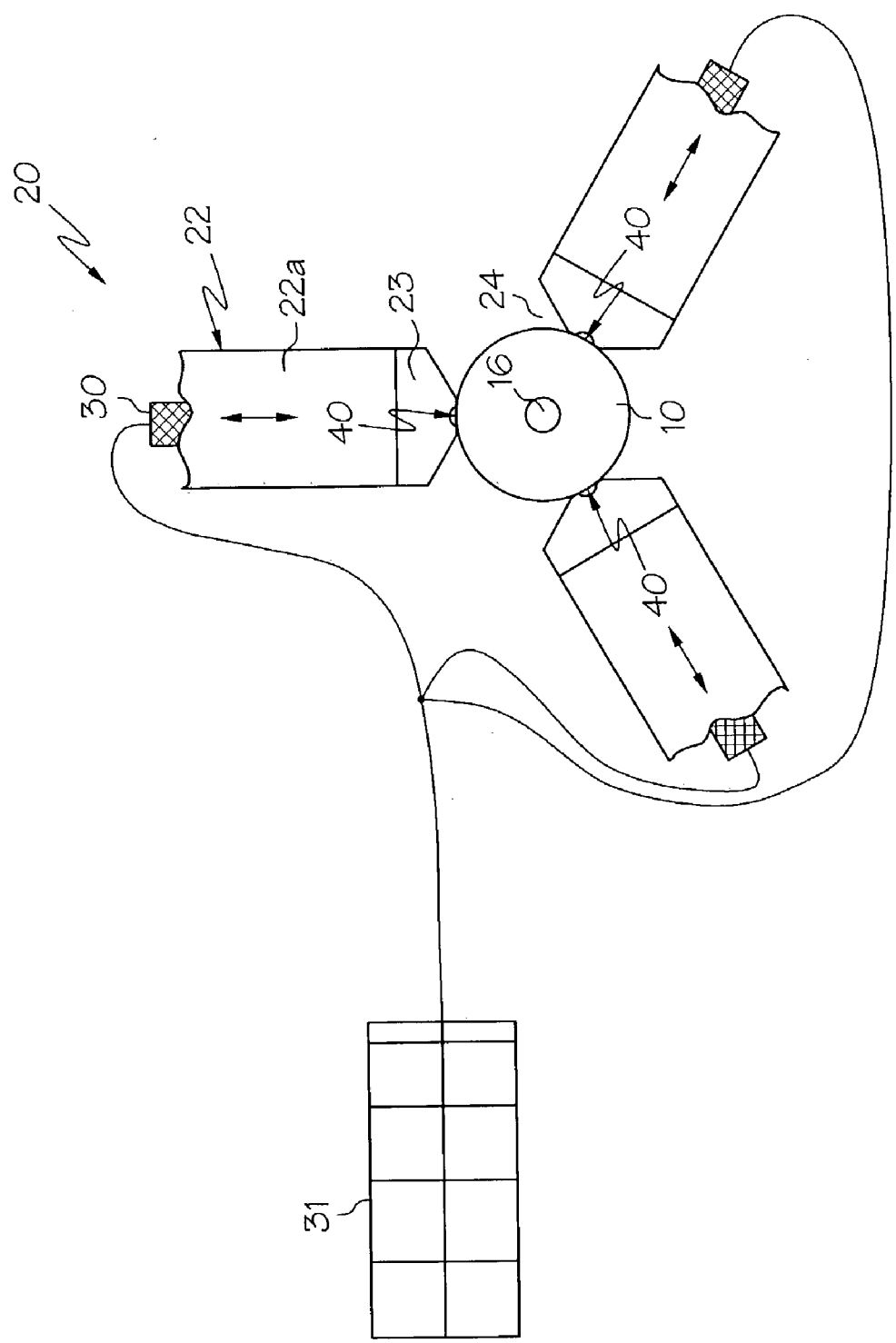
FIG. 3 is a cross-sectional view of the embodiment illustrated in FIG. 2 shown with a balloon positioned therein.
Figure 4:
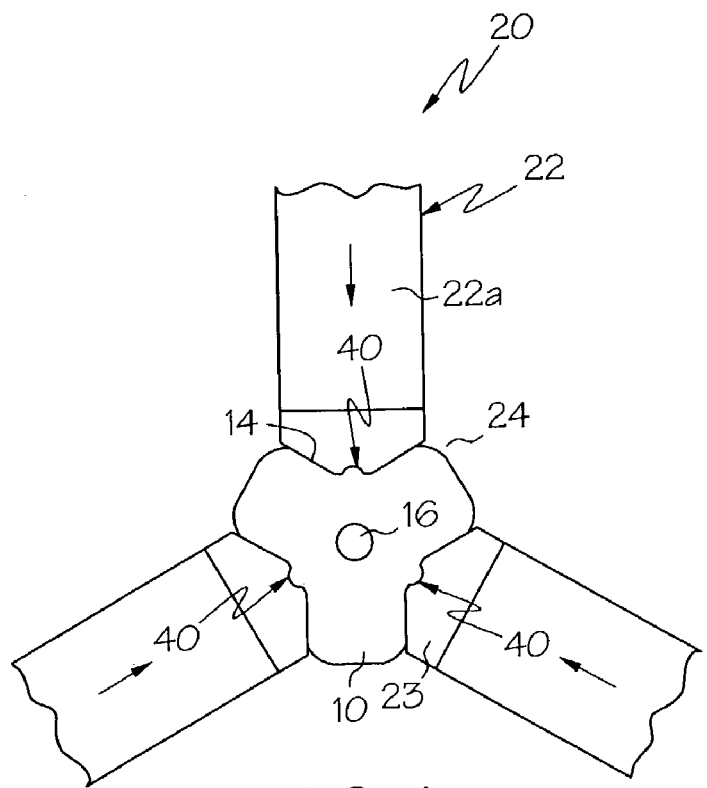
FIG. 4 is a cross-sectional view of the apparatus illustrated in FIG. 3 shown during the wing formation process.
Figure 5:
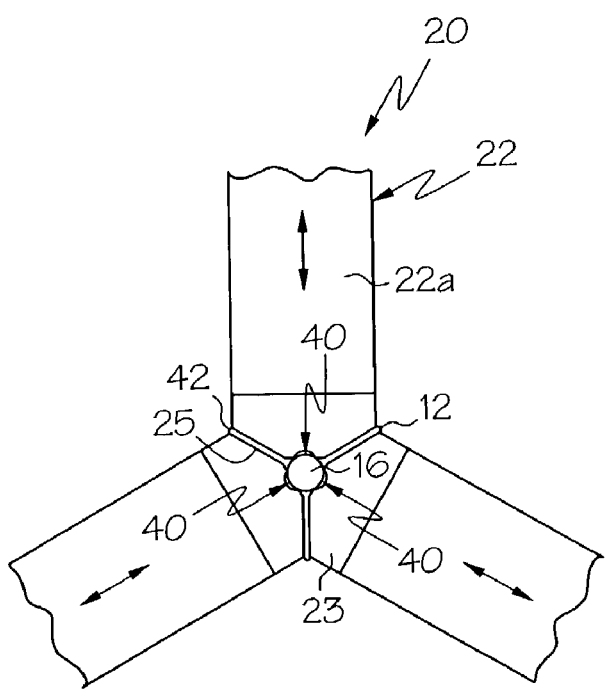
FIG. 5 is a cross-sectional view of the apparatus illustrated in FIG. 4 shown during the wing formation process.

In at least one embodiment of the invention a method of forming balloon wings is accomplished through the use of a balloon folding apparatus, indicated generally at 20 in FIG. 2. The apparatus 20 comprises a plurality of moveable members 22. In the embodiment shown in FIGS. 2–5 members 22 are characterized as moveable blades 22a, whereas in the embodiment shown in FIGS. 6–8 members 22 are inflatable members 22b. Members 22 are uniformly disposed about a receiving area 24. In FIGS. 2–5 blades 22a are constructed and arranged to be moved in a radial direction into the receiving area 24 as well as out of the receiving area 24. A catheter balloon 10 is positioned within receiving area 24 when the blades are in the open position such as is shown in FIG. 3. The balloon 10 is partially inflated under a pressure of about 20–40 p.s.i. In some embodiments the balloon is inflated to about 30 p.s.i. As is shown in FIG. 4, once the balloon catheter 10 is positioned into the receiving area, the blades 22a are moved radially inward to push against the outside surface 14 of the balloon 10. As the blades 22a push against the balloon catheter 10, portions of the balloon are forced radially outward away from the catheter shaft 16 to form wings 12. When the blades 22a are in their fully closed position about the catheter shaft 16, such as is shown in FIG. 5, the wings 12 are fully formed between adjacent blades 22a.

In the various embodiments shown herein, the folding apparatus 20 includes one or more transducers 30 which are functionally engaged to one or more of the members 22 and/or other portions of the apparatus 20, such as shown in FIGS. 2–3 and 6–8. Transducers 30 transmit vibratory energy in order to impart vibrations to the apparatus 20.

The vibrations produced by the transducers 30 may be of any frequency, but in at least one embodiment the vibrations are in the ultrasonic range. Ultrasonic vibratory energy may provide a uniform or non-uniform vibration to a selected portion of a member 22. In some embodiments the transducers 30 may provide ultrasonic energy in a frequency that can range from less than about 1,000 kiloHertz.

In some embodiments transducers 30 may be piezoelectric transducers that are engaged to an ultrasonic generator 31 such as is shown in FIGS. 2–3. The generator 31 provides electrical energy to the transducers 30. The transducers 30 then convert the electrical energy to mechanical energy in the form of vibrations.

In some embodiments, an example of which is shown in FIG. 2, the transducers 30 and/or another component of the apparatus 20 may include a heating element 33 which heats one or more portions of the members 22. In some embodiments the transducers 30 may emit vibratory energy which not only imparts vibrations to at least a portion of the members 22 and balloon 10, but which also acts to heat at least a portion of the members 22 and balloon 10. In some embodiments heating the balloon material during the wing forming process will aid in forming the wings 12 by softening the balloon material to allow for an improved creased fold.

By applying vibratory energy to the vibrating members 22, the vibratory energy is communicated to the balloon 10 during the wing forming process. Vibration of the members 22 and balloon 10 results in a reduced frictional interface between the members 22 and balloon 10.

As is shown in FIGS. 3–5, the reduction in friction between blades 22a and balloon 10, as blades 22a push segments 40 of the balloon 10 radially inward during formation of wings 12, the material of the wings 12 more easily slides over the balloon contacting portion 23 of the blades 22a and into the space 25 between each blade 22a. The reduction in friction and resistance between balloon contacting portions 23 and balloon 10 allows the wings 12 to be formed with lower risk of balloon damage which may otherwise result from the interface of balloon 10 and blades 22a.

To further improve the performance of the apparatus 10, balloon contacting portions 23 of the blades 22a is at least partially constructed of a relatively soft material such as Silicone, natural or synthetic polymers, etc. The remaining portion of each blade 22a may be constructed of metal and/or other materials.

With less friction between the balloon 10 and blades 22a, there is less chance of the balloon material inconsistently gripping the balloon contacting portions 23 of the blades 22a as the blades 22a move inward against the balloon 10. As a result, in some embodiments the application of vibratory energy to the balloon 10 will aid in providing a balloon that has wings of substantially the same uniform length, such as is shown in FIG. 1.

Figure 6:
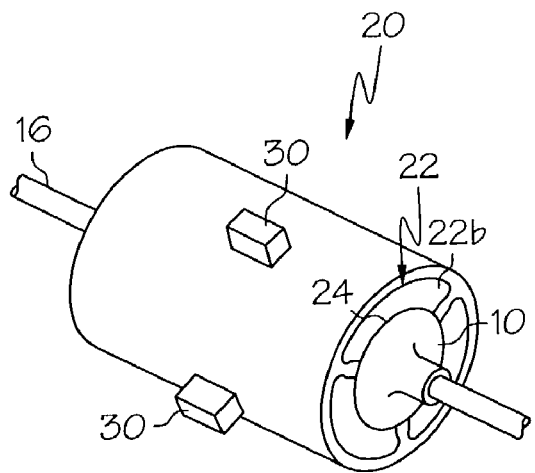
FIG. 6 is a perspective view of an embodiment of the invention shown with a balloon positioned therein.
Figure 7:
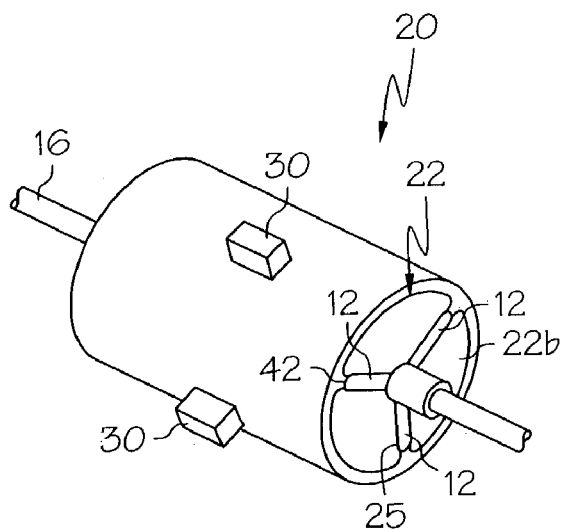
FIG. 7 is a perspective view of the apparatus illustrated in FIG. 6 shown during the wing formation process.
Figure 8:
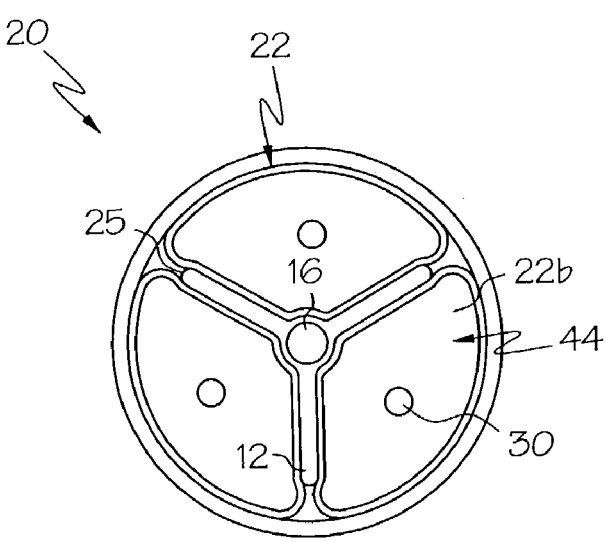
FIG. 8 is a cross-sectional view of an embodiment of the invention shown during the wing formation process.

In an alternative embodiment of the invention shown in FIGS. 6–7, the members 22 of the apparatus 20 are characterized as inflatable members 22b rather than moveable blades 22a, such as are shown in FIGS. 2–5. Inflatable members 22b are inflatable from an uninflated state shown in FIG. 6 to a fully inflated state shown in FIG. 7. When the inflatable members 22b are inflated, the members 22b increase in diameter thereby directing an inward acting force against the balloon 10 that is positioned within the receiving region 24. When the members 22b are fully inflated the wings 12 are sandwiched between the adjacent fully inflated members 22b. Transducers 30 may be engaged to any region of the members 22b. Alternatively, the members 22b may be disposed about the transducer 30 such as is shown in FIG. 8. In the embodiment shown in FIG. 8, the vibratory energy emitted from the transducers 30 is passed through an inflation media 44 to the members 22b and eventually to the balloon 10.

In addition to reducing the risk of damage to balloon 10, the application of vibratory energy to the members 22 and balloon 10 also improves the profile and crease characteristics of the wings 12. As is shown in FIGS. 5, 7 and 8, when the members 22 are in the fully closed position, the wings 12 are positioned with in the space 25 between adjacent members 22. During the wing formation process the members 22 push inward against segments 40 of the balloon 10 causing the material of the wings 12 to be pushed outward into the spaces 25 between the members 22. When the members are fully closed, each wing is compressed between adjacent members 22 to form a crease 42 along their respective outside edges.

In some embodiments, application of vibrations to the members 22 and wings 12 helps to provide each wing with a well defined crease 42 that extends through the length of the entire balloon 10 such as is shown in FIG. 9. In at least one embodiment, vibrating the balloon 10 when the apparatus is closed assists in forming a crease through the body 50 of the balloon as well as in the adjacent cone regions 52 and 54. Providing a crease 42 that extends through all portions of the balloon aids in forming flatter more easily folded wings 12.

In addition, by providing cone regions 52 and 54 with improved creasing, the folded balloon profile over the cones may be decreased. This reduction reduces the risk of damaging the balloon while positioning a stent onto the balloon. The reduction in cone profile also allows a catheter equipped with such a balloon to cross lesion sights with greater ease. Finally, by providing a balloon with improved body and cone creasing the forces necessary to crimp a stent or other medical device to the balloon may be reduced.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of shaping a medical balloon, the method comprising:
   applying a radially inward force to at least a portion of the medical balloon; and
   vibrating the at least a portion of the medical balloon.

2. The method of claim 1, wherein the radially inward force is applied to the at least a portion of a medical balloon at substantially the same time as at least a portion of a medical balloon is vibrated.

3. The method of claim 1, wherein the at least a portion of a medical balloon is vibrated ultrasonically.

4. The method of claim 1 wherein the medical balloon is disposed about a catheter shaft.

5. The method of claim 1 wherein the radially inward force is applied to a plurality of longitudinal segments of the medical balloon.

6. The method of claim 5 wherein the balloon comprises a body region positioned between a first cone region and a second cone region, the plurality of longitudinal segments extending substantially through the first cone region, the body and the second cone region.

7. The method of claim 6 wherein application of the inward radial force deforms the plurality of longitadinal. segments of the balloon to form a plurality of wings.

8. The method of claim 1 further comprising the step of heating at least a portion of the medical balloon.

9. The method of claim 1 wherein the at least a portion of the medical balloon is vibrated at at least one frequency selected from the group consisting of: harmonic frequencies, subharmonic frequencies, ultrasonic frequencies and any combination thereof.

10. The method of claim 1 wherein the at least a portion of the medical balloon is vibrated at multiple frequencies.

* * * * *